US009952391B2

(12) United States Patent
Sakai et al.

(10) Patent No.: US 9,952,391 B2
(45) Date of Patent: Apr. 24, 2018

(54) OPTICAL TRANSMISSION MODULE, ENDOSCOPE, AND METHOD FOR MANUFACTURING OPTICAL TRANSMISSION MODULE

(71) Applicant: OLYMPUS CORPORATION, Tokyo (JP)

(72) Inventors: Youhei Sakai, Ina (JP); Yusuke Nakagawa, Nagano (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/710,134

(22) Filed: Sep. 20, 2017

(65) Prior Publication Data
US 2018/0008132 A1  Jan. 11, 2018

Related U.S. Application Data

(63) Continuation of application No. PCT/JP2015/058448, filed on Mar. 20, 2015.

(51) Int. Cl.
*G02B 6/36* (2006.01)
*G02B 6/34* (2006.01)
(Continued)

(52) U.S. Cl.
CPC ............ *G02B 6/4214* (2013.01); *A61B 1/045* (2013.01); *A61B 1/05* (2013.01); *A61B 1/06* (2013.01); *G02B 6/12* (2013.01); *G02B 6/42* (2013.01)

(58) Field of Classification Search
CPC . G02B 6/12; G02B 6/13; G02B 6/138; G02B 6/12004; G02B 6/12007;
(Continued)

(56) References Cited

U.S. PATENT DOCUMENTS 6,987,906 B2 *  1/2006  Nakama ............ G02B 6/12004
385/15
2009/0169216 A1  7/2009  Hiruta

FOREIGN PATENT DOCUMENTS

JP    H02-062502 A    3/1990
JP    H05-173045 A    7/1993
(Continued)

OTHER PUBLICATIONS

International Search Report dated Jun. 2, 2015 received in PCT/JP2015/058448.

*Primary Examiner* — Akm Enayet Ullah
*Assistant Examiner* — Michael Mooney
(74) *Attorney, Agent, or Firm* — Scully, Scott, Murphy & Presser, P.C.

(57) ABSTRACT

An optical transmission module includes a light emitting device for transmitting a first optical signal, a light receiving device for receiving a second optical signal, an optical fiber for guiding a third optical signal in which the first optical signal and the second optical signal are coupled, and an optical waveguide substrate having an optical waveguide made of first resin, wherein a groove formed on the optical waveguide substrate is provided with a prism having the optical fiber and a reflective face through which the first optical signal transmit, a first side face of the prism contacts a first wall face of the groove, and a second side face thereof contacts a second wall face of the groove.

12 Claims, 9 Drawing Sheets

(51) Int. Cl.
  *G02B 6/12* (2006.01)
  *G02B 6/42* (2006.01)
  *A61B 1/05* (2006.01)
  *A61B 1/06* (2006.01)
  *A61B 1/045* (2006.01)

(58) Field of Classification Search
  CPC .......... G02B 6/26; G02B 6/42; G02B 6/4214;
       G02B 6/4246; G02B 6/43; G02B
       2006/12104; A61B 1/045; A61B 1/05;
       A61B 1/06; H05K 1/0274
  USPC .................. 385/14, 15, 36, 88–93, 131–132
  See application file for complete search history.

(56) References Cited

FOREIGN PATENT DOCUMENTS

| | | |
|---|---|---|
| JP | H06-151903 A | 5/1994 |
| JP | 2008-250007 A | 10/2008 |
| JP | 2009-162882 A | 7/2009 |
| JP | 2012-113031 A | 6/2012 |

\* cited by examiner

OPTICAL TRANSMISSION MODULE, ENDOSCOPE, AND METHOD FOR MANUFACTURING OPTICAL TRANSMISSION MODULE

CROSS REFERENCE TO RELATED APPLICATION

This application is a continuation application of PCT/JP2015/058448 filed on Mar. 20, 2015, the entire contents of which are incorporated herein by this reference.

BACKGROUND OF THE INVENTION

1. Field of the Invention

The present invention relates to an optical transmission module including a wiring board mounted with a plurality of optical devices thereon, and a polymer-type optical waveguide substrate whose main surface is bonded to the wiring board, an endoscope having the optical transmission module, and a method for manufacturing the optical transmission module.

2. Description of the Related Art

An electronic endoscope has an image pickup device such as a CCD at a distal end portion of an elongated insertion portion. In recent years, the use of high-resolution image pickup device to an endoscope has been increased. Since when a high-resolution image pickup device is used, signals to be transmitted from the image pickup device to a signal processing apparatus (processor) increase, there is preferably employed optical signal transmission via a thin optical fiber instead of electric signal transmission via a metal wiring. Further, by use of a bidirectional optical communication technique, it is possible to transmit not only image data but also clock signals and the like from the signal processing apparatus to the image pickup device through one optical fiber. With the bidirectional optical communication technique, a first optical signal generated by a light emitting device and a second optical signal received by a light receiving device are coupled/branched by an optical transmission module.

JP 2008-250007 A discloses a polymer-type optical waveguide substrate whose upper surface is bonded to a wiring board mounted with an optical device thereon. A groove with a tilt face of 45 degrees, which is formed on the optical waveguide substrate by use of a dicing blade, is bonded with a mirror block with a mirror for optically coupling an optical path of the optical device and an optical path of an optical waveguide.

JP 5-173045 A discloses an optical semiconductor module in which an optical device, a prism, and the like are arranged at predetermined positions on a silicon substrate and a groove as optical path is formed thereon.

SUMMARY OF THE INVENTION

An optical transmission module according to an embodiment of the present invention includes a first optical device for transmitting or receiving a first optical signal, a second optical device for transmitting or receiving a second optical signal, an optical fiber for guiding a third optical signal in which the first optical signal and the second optical signal are coupled, and an optical waveguide substrate having an optical waveguide made of first resin, in which the optical waveguide has a first reflective face with a tilt angle of 45 degrees relative to a first end face, and a second end face is optically coupled with an optical path of the optical fiber, wherein a groove formed on the optical waveguide substrate is provided with the optical fiber and a prism having a second reflective face with a tilt angle of 45 degrees through which the first optical signal transmits, an optical path of the optical waveguide is optically coupled with an optical path of the first optical device orthogonal to the optical path of the optical waveguide via the first reflective face, the optical path of the optical fiber is optically coupled with an optical path of the second optical device orthogonal to the optical path of the optical fiber via the second reflective face, the second end face of the optical waveguide is exposed on a first wall face of the groove, a face of a positioning member made of the first resin is exposed on a second wall face of the groove, a first side face of the prism contacts the first wall face of the groove, and a second side face contacts the second wall face of the groove.

An endoscope according to another embodiment of the present invention includes an optical transmission module at a distal end portion of an insertion portion, the optical transmission module including a first optical device for transmitting or receiving a first optical signal, a second optical device for transmitting or receiving a second optical signal, an optical fiber for guiding a third optical signal in which the first optical signal and the second optical signal are coupled, and an optical waveguide substrate having an optical waveguide made of first resin, in which the optical waveguide has a first reflective face with a tilt angle of 45 degrees relative to a first end face, and a second end face is optically coupled with an optical path of the optical fiber, wherein a groove formed on the optical waveguide substrate is provided with the optical fiber and a prism having a second reflective face with a tilt angle of 45 degrees through which the first optical signal transmits, an optical path of the optical waveguide is optically coupled with an optical path of the first optical device orthogonal to the optical path of the optical waveguide via the first reflective face, the optical path of the optical fiber is optically coupled with an optical path of the second optical device orthogonal to the optical path of the optical fiber via the second reflective face, the second end face of the optical waveguide is exposed on a first wall face of the groove, a face of a positioning member made of the first resin is exposed on a second wall face of the groove, a first side face of the prism contacts the first wall face of the groove, and a second side face contacts the second wall face of the groove.

There is further provided a method for manufacturing the optical transmission module according to still another embodiment of the present invention, the optical transmission module including a first optical device for transmitting or receiving a first optical signal, a second optical device for transmitting or receiving a second optical signal, an optical fiber for guiding a third optical signal in which the first optical signal and the second optical signal are coupled, and an optical waveguide substrate having an optical waveguide made of first resin, in which the optical waveguide has a first reflective face with a tilt angle of 45 degrees relative to a first end face, and a second end face is optically coupled with an optical path of the optical fiber, wherein a groove formed on the optical waveguide substrate is provided with the optical fiber and a prism having a second reflective face with a tilt angle of 45 degrees through which the first optical signal transmits, an optical path of the optical waveguide is optically coupled with an optical path of the first optical device orthogonal to the optical path of the optical waveguide via the first reflective face, the optical path of the optical fiber is optically coupled with an optical path of the second optical device orthogonal to the optical path of the optical fiber via the second reflective face, the second end face of the optical waveguide is exposed on a first wall face of the groove, a face of a positioning member made of the first resin is exposed on a second wall face of the groove, a first side face of the prism contacts the first wall face of the groove, a second side face contacts the second wall face of the groove, and the optical waveguide and the positioning member are patterned at a same time by the photolithography method.

DETAILED DESCRIPTION OF THE PREFERRED EMBODIMENT(S)

First Embodiment

<Configuration of Optical Transmission Module 1>

Figure 2:
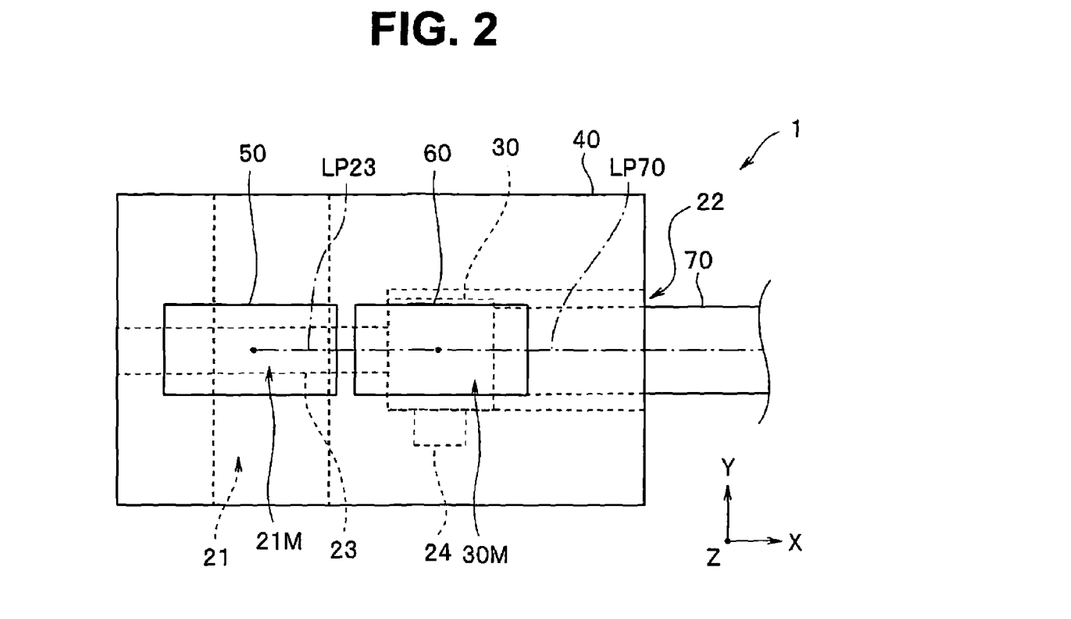
FIG. 2 is a top view of the optical transmission module according to the first embodiment.
Figure 3:
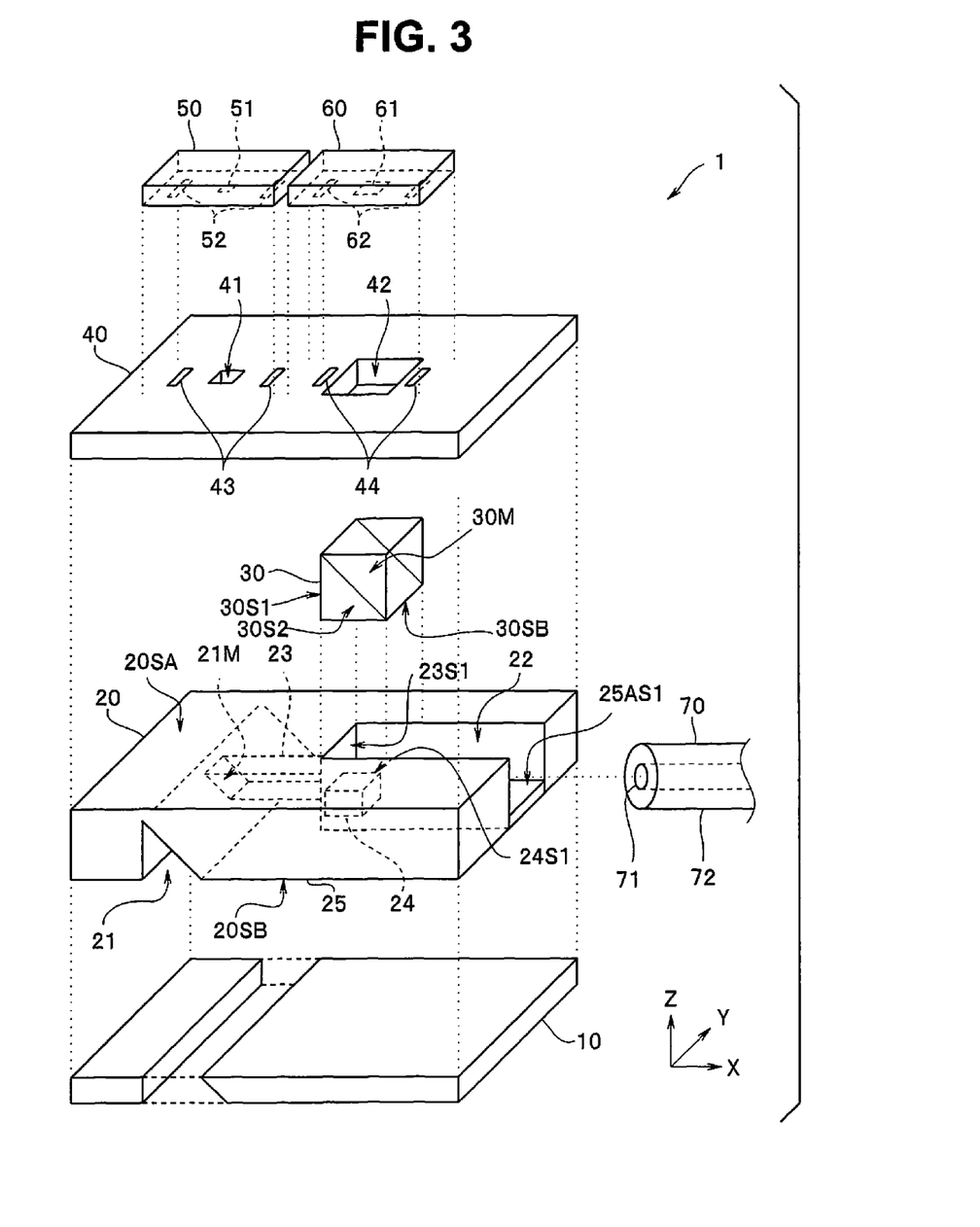
FIG. 3 is an exploded view of the optical transmission module according to the first embodiment.

An optical transmission module 1 according to a first embodiment will be described with reference to FIG. 1 to FIG. 3. In the following description, it is noted that the figures according to each embodiment are schematic and a relationship between thickness and width in each part, and a ratio of thicknesses in respective parts, and the like are different from actual ones, and a relationship or ratio of mutual dimensions may be different between the figures. Further, some components (such as bonding layer) are not illustrated. In the following, the increasing direction on the Z axis in the drawings is denoted as upward direction, and the decreasing direction on the Z axis is denoted as downward direction.

The optical transmission module 1 includes a light emitting device 50 as first optical device, a light receiving device 60 as second optical device, an optical waveguide substrate 20, a prism 30, and an optical fiber 70. A first substrate mounted with the light emitting device 50 and the light receiving device 60 thereon (which will be denoted as "wiring board" below) 40, and a second substrate 10 are arranged on an upper surface 20SA of the optical waveguide substrate 20 and a lower surface 20SB thereof, respectively.

In the optical transmission module 1, the optical fiber 70 guides a third optical signal in which a first optical signal with a first wavelength $\lambda 1$ transmitted by the light emitting device 50 is coupled with a second optical signal with a second wavelength $\lambda 2$ different from the first wavelength $\lambda 1$ received by the light receiving device 60. For example, the first wavelength $\lambda 1$ is 850 nm, and the second wavelength $\lambda 2$ is 1300 nm.

The light emitting device 50 is a vertical cavity surface emitting laser (VCSEL), and outputs a light of an optical signal in the vertical direction (Z-axis direction) relative to a light emitting face (XY surface) depending on an input drive electric signal. For example, the micro-light emitting device 50 with a plan view dimension of 250 μm×300 μm has, on the light emitting face, a light emitting part 51 with a diameter of 20 μm and connection terminals 52 electrically connected to the light emitting part 51 and directed for supplying an electric signal.

The light receiving device 60 is formed of a photodiode (PD), and converts an optical signal incident in the vertical direction (Z-axis direction) relative to a light receiving face to an electric signal and outputs the electric signal. For example, the micro-light receiving device 60 with a plan view dimension of 350 μm×300 μm has, on the light receiving face, a light receiving part 61 with a diameter of 50 μm and connection terminals 62 electrically connected to the light receiving part 61 and directed for outputting a received electric signal.

The optical waveguide substrate 20 is a polymer-type optical waveguide substrate in which a clad 25 surrounds a core 23 as optical waveguide with the X-axis direction in which an optical signal is guided as longitudinal direction. The polymer-type optical waveguide substrate 20, in which the core 23 and the clad 25 are made of resin, is easier to machine and more excellent in flexibility than an optical waveguide substrate made of inorganic material such as quartz. Further, the optical transmission module 1 in which the first substrate 40 and the second substrate 10, which are flexible, sandwich the flexible optical waveguide substrate 20 is flexible and is easy to arrange in a small space. That is, it is preferable that the first substrate 40 and the second substrate 10 are flexible.

The core 23 as optical waveguide is made of first resin, and the clad 25 is made of second resin with a lower refractive index than the first resin. As described below, the clad 25 is formed of a lower clad 25A provided below the core 23 and an upper clad 25B surrounding the side and the top of the core 23.

The optical waveguide substrate 20 is such that a positioning member 24 made of the same first resin as the core 23 is provided in plane with the core 23. As described below, the core 23 and the positioning member 24 are manufactured at the same time with patterning a core sheet 23S (see FIG. 5A).

The light emitting device 50 and the light receiving device 60 are electrically connected with electrode pads 43 and 44 of the wiring board 40, respectively. The wiring board 40 is provided with a throughhole 41 as optical path LP50 for the first optical signal and a throughhole 42 as optical path LP60 for the second optical signal. When the wiring board 40 is high in optical transmittance and attenuation in optical signal is in a permitted range, the throughholes 41 and 42 do not need to be formed.

The optical waveguide substrate 20 is formed with a groove 22 in which the long-axis direction is parallel with the long-axis direction of the core 23 and the cross-section orthogonal to the long-axis is rectangular. The groove 22 is such that the upper surface is opened and the bottom surface is an upper surface 25AS1 of the lower clad 25A. The groove 22 is such that a second end face 23T2 of the core is exposed on a first wall face 23S1 (see FIG. 3). When the upper surface is bonded with the wiring board 40, the groove 22 becomes a hole with either side opened.

On the other hand, a first reflective face 21M with a tilt angle of 45 degrees is formed on a first end face 23T1 opposing the second end face 23T2 of the core 23. The first reflective face 21M is a tilt face of a groove 21 formed from the lower surface by use of a dicing blade. The first reflective face 21M reflects a light incident into the core 23 in the vertical direction (Z-axis direction) by 90 degrees, and guides it in the longitudinal direction (X-axis direction) of the core 23.

The core 23 may be further extended from the first end face 23T1 during manufacture. However, when the groove 21 is formed, the outside of the first reflective face 21M does not function as optical waveguide, and thus the first reflective face 21M is to be an end face of the core 23 as optical waveguide.

The wall face of the groove 21, particularly the first reflective face 21M may be formed with a reflective film made of metal such as gold in order to enhance the reflectivity, and the inside of the groove 21 may be filled with resin.

On the other hand, the groove 22 is provided with the prism 30 and the optical fiber 70. The prism 30 is substantially cuboid in plan view of rectangle, and has a second reflective face 30M with a tilt angle of 45 degrees. The second reflective face 30M transmits the first optical signal with the first wavelength, but reflects the optical path of the second optical signal with the second wavelength. That is, the prism 30 is a dichroic right-angle prism with the reflective face 30M having a property of transmitting a light with the wavelength λ1 and reflecting a light with the wavelength As illustrated in FIG. 1, the first substrate (wiring board) 40 mounted with the light emitting device 50 and the light receiving device 60 thereon is provided on the upper surface of the optical waveguide substrate 20. Then, the first substrate 40 and the optical waveguide substrate 20 are positioned such that the light emitting device 50 and the light receiving device 60 are immediately above the core 23.

The first optical signal output (transmitted) by the light emitting device 50 in parallel with the Z axis is reflected on the first reflective face 21M in parallel with the X axis, and is guided to the core 23. In other words, the first reflective face 21M optically couples the optical path LP50 of the light emitting device 50 orthogonal to an optical path LP23 of the core 23 as waveguide with the optical path LP23. The first optical signal passes through the second reflective face 30M to be incident into the optical fiber 70.

On the other hand, the second optical signal guided by the optical fiber 70 in parallel with the X axis is reflected on the second reflective face 30M in parallel with the Z axis, and is incident into and received by the light receiving part 61 of the light receiving device 60. In other words, the second reflective face 30M optically couples the optical path LP60 of the light receiving device 60 orthogonal to an optical path LP70 of the optical fiber 70 with the optical path LP70 of the optical fiber 70.

Then, the two side faces (30S1 and 30S2) of the prism 30 contact the first wall face 23S1 (see FIG. 3) of the groove 22 or a second wall face 24S1 (see FIG. 3) orthogonal to the first wall face 23S1 so that the prism 30 provided in the groove 22 is defined at a position in the inplane direction (XY direction). The bottom surface 30SB contacts the upper surface 25AS1 of the lower clad 25A so that the prism 30 is defined at a position in the vertical direction (Z direction).

The second wall face 24S1 is a face of the positioning member 24 made of the first resin. The two side faces (30S1 and 30S2) and the bottom surface 30SB are defined in their positions, and thus the prism 30 is accurately arranged at a predetermined position. Thus, the optical transmission module 1 is excellent in optical transmission efficiency.

<Method for Manufacturing Optical Transmission Module 1>

Figure 4:
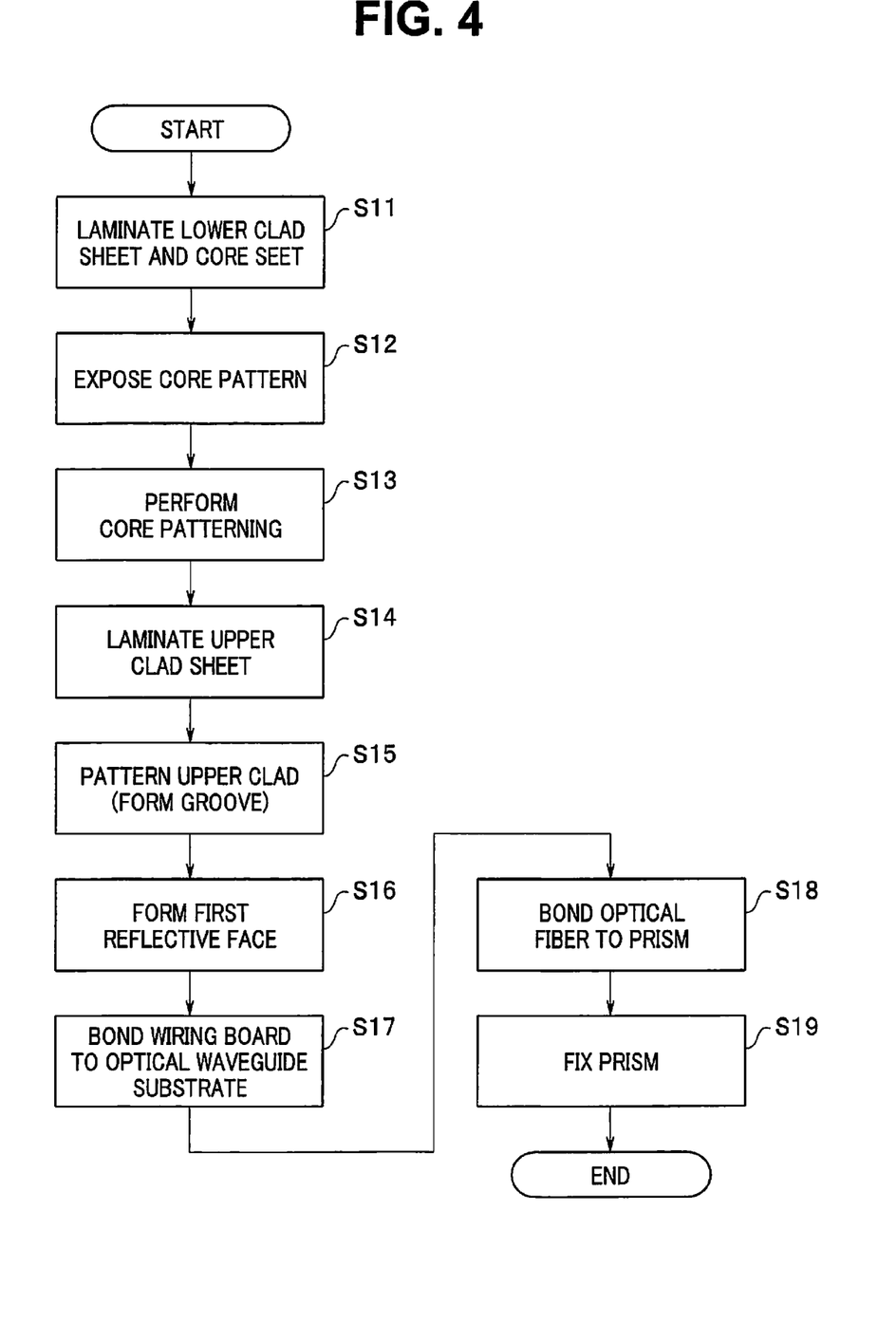
FIG. 4 is a flowchart for explaining a method for manufacturing the optical transmission module according to the first embodiment.

A method for manufacturing the optical transmission module 1 will be described below with reference to the flowchart of FIG. 4

<Step S11>

A lower clad sheet 25AS is laminated on the second substrate 10. The second substrate 10 employs a FPC substrate, ceramic substrate, glass epoxy substrate, glass substrate, silicon substrate, or the like, and is preferably a flexible substrate. The second substrate 10 is a support substrate for manufacturing the optical waveguide substrate 20, and is not an essential component for the optical transmission module 1. Further, the second substrate 10 may be a wiring board with a wiring, or an electrode board connected with a ground potential line and covered with a conductive film.

When the lower clad sheet 25AS is weak in adhesiveness with the second substrate 10, a bonding layer may be provided therebetween.

Figure 5A:
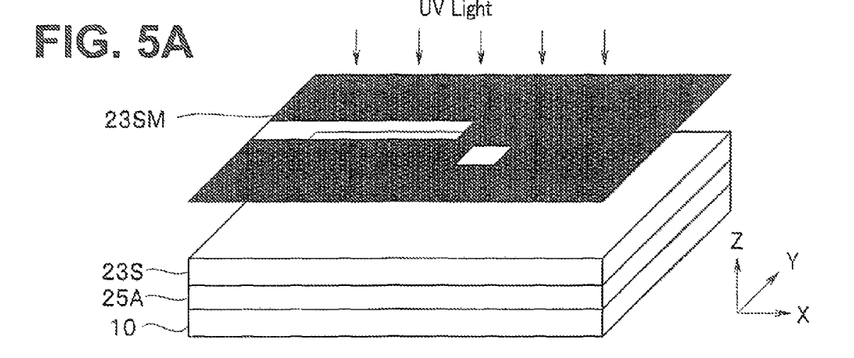
FIG. 5A is a perspective view for explaining the method for manufacturing the optical transmission module according to the first embodiment.
Figure 5B:
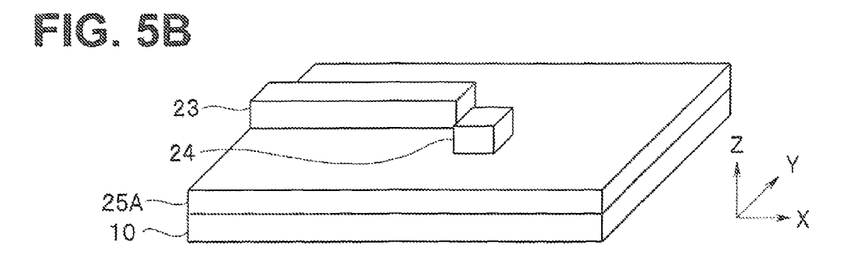
FIG. 5B is a perspective view for explaining the method for manufacturing the optical transmission module according to the first embodiment.
Figure 5C:
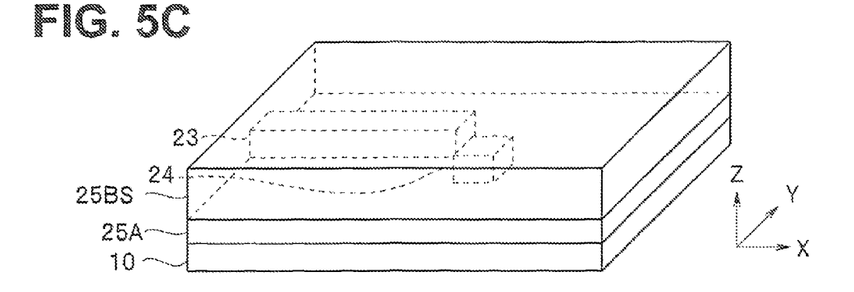
FIG. 5C is a perspective view for explaining the method for manufacturing the optical transmission module according to the first embodiment.

The lower clad sheet 25AS is a film made of the same second resin as an upper clad sheet 25BS (see FIG. 5C). The second resin has a lower refractive index than the first resin making the core 23. The lower clad sheet 25AS is not patterned, but the second resin used for the upper clad sheet 25BS to be patterned preferably contains (A) base polymer, (B) photopolymerized compound, and (C) photopolymerization initiator. The lower clad 25A and the upper clad 25B have only to have the functions of the clad 25, respectively, and do not necessarily need to be made of the same resin. For example, the lower clad sheet 25AS may not contain a photopolymerized compound and a photopolymerization initiator.

Base polymer is directed for securing the mechanical intensity of the clad, and is made of highly-transparent resin such as high-purity polyimide-based resin or polyether-based resin. Photopolymerized compound is not particularly limited, and may be any compound polymerized by irradiation with light such as ultraviolet ray, such as (meta)acrylate. Photopolymerization initiator is not particularly limited, and may be aryldiazonium salt when the photopolymerized compound is an epoxy compound, for example.

Additionally, any additive such as antioxidant, antiyellowing agent, ultraviolet absorber, visible light absorber, colorant, plasticizer, stabilizer, and filler may be added to the resin as needed at a rate at which the effects of the present invention are not influenced.

According to the present embodiment, polyimide fluoride resin with a refractive index of 1.40 to 1.75, which is excellent in heat resistance, transparency, and isotropy, is used as base polymer.

The lower clad sheet 25AS is manufactured by dissolving the composition into a solvent, applying it on a support film, and removing the solvent.

The lower clad sheet 25AS and the upper clad sheet 25BS (see FIG. 5C) preferably have a thickness of 5 µm to 500 µm. When the thickness is 5 µm or more, a thickness of the clad required for confining a light can be secured, and when the thickness is 500 µm or less, a thickness can be easily uniformed.

The lower clad sheet 25AS is laminated and then hardened by irradiation with ultraviolet ray to be the lower clad 25A. The material of the lower clad sheet 25AS may be only non-photosensitive base polymer.

Then, the core sheet 23S made of the first resin, which is to be the core 23 and the positioning member 24, is laminated on the lower clad 25A. The first resin is higher in refractive index than the second resin, and can be patterned. For example, the first resin has substantially the same composition as the second resin, and is controlled in refractive index by molecular weight, the amount of additive, or the like. According to the present embodiment, the first resin and the second resin are made of the same polyimide, but the refractive index of the first resin is 1.555 and the refractive index of the second resin is 1.537.

The thickness of the core sheet 23S is the height of the core 23 as optical waveguide. The thickness of the core sheet 23S is preferably between 5 µm and 100 µm in order to secure the optical guiding property.

<Step S12>FIG. 5A

An ultraviolet ray is emitted (exposed) on the core sheet 23S via a negative photomask 23SM.

The photomask 23SM is a negative mask in which the areas corresponding to the shapes of the core 23 and the positioning member 24 are transparent. Therefore, an ultraviolet ray is emitted only on the areas to be the core 23 and the positioning member 24, and the first resin in the areas is polymerized.

<Step S13>FIG. 5B

The first resin in the area on which an ultraviolet ray is not emitted is dissolved by a development processing so that the core 23 and the positioning member 24 are formed at the same time.

In the method for manufacturing the optical transmission module 1, the core 23 and the positioning member 24 are patterned at the same time by the photolithography method.

The patterning step is not limited to the direct exposure method, and may employ the selective polymerization method, the reactive ion etching (RIE) method, or the photo-bleaching method.

A dimension accuracy of the photomask is high, and thus a relative position relationship between the core 23 and the positioning member 24 is accurately defined.

The core 23 as optical waveguide has a width of 5 µm to 100 µm. As long as the positioning member 24 has the side face 24S1 orthogonal to the second end face 23S1 of the core 23 at a predetermined position, shapes of other parts are not particularly limited.

The core sheet 23S made of the first resin, which is provided on a carrier film made of polyethylene terephthalate or the like and having flexibility and toughness, is patterned and then transferred on the lower clad 25A thereby to provide the core 23 and the positioning member 24 thereon.

<Step S14>FIG. 5C

The upper clad sheet 25BS is laminated. A lower limit of the thickness of the upper clad sheet 25BS needs to be over a value [sum of the thickness of the core sheet 23S and the thickness of the lower clad sheet 25AS] in order to cover the core 23. The thickness of the upper clad sheet 25BS is preferably a value [the lower limit+10 µm to 100 µm] or less. For example, when the thickness of the lower clad sheet 25AS is 30 µm and the thickness of the core sheet 23S is 25 µm, the lower limit of the upper clad sheet 25BS is 55 µm, but preferably between 65 µm and 155 µm.

Figure 5D:
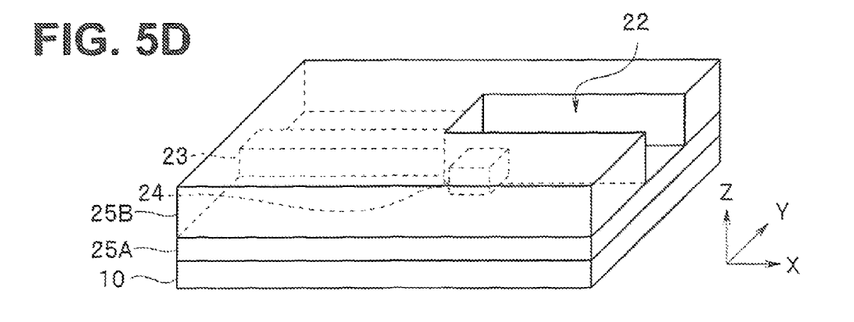
FIG. 5D is a perspective view for explaining the method for manufacturing the optical transmission module according to the first embodiment.

<Step S15>FIG. 5D

The upper clad sheet 25BS is patterned in order to form the predetermined groove 22 on the upper clad 25B. For example, the groove 22 is formed by the direct exposure method using a negative photomask.

Figure 5E:
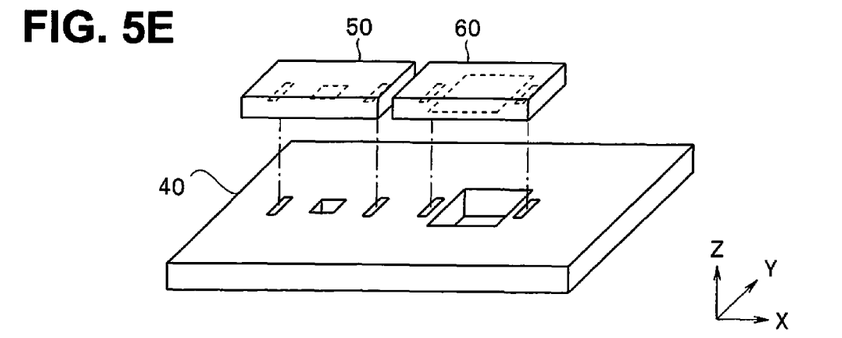
FIG. 5E is a perspective view for explaining the method for manufacturing the optical transmission module according to the first embodiment.

Additionally, as illustrated in FIG. 5E, the light emitting device 50 and the light receiving device 60 are surface-mounted on the first substrate (first wiring board) 40. That is, the light emitting device 50 is flip-chip mounted on the first substrate 40 while the light emitting part 51 is arranged to oppose the throughhole 41 of the first substrate 40. The light receiving device 60 is flip-chip mounted on the first substrate 40 while the light receiving part 61 is arranged to oppose the throughhole 42 of the first substrate 40.

For example, the Au bumps as the connection terminals 52 of the light emitting device 50 are ultrasonically bonded with the electrode pads 43 of the first substrate 40. A sealing agent such as underfill material or side-fill material may be injected into the boded parts. After solder paste or the like is printed on the first substrate 40 and the light emitting device 50 is arranged at a predetermined position, the solder may be melted and mounted by reflow or the like. Similarly, the connection terminals 62 of the light receiving device 60 are bonded to the electrode pads 44 of the first substrate 40.

<Step S16>

On the other hand, the V-groove 21 is formed by use of a dicing blade from the lower surface (the second substrate) of the optical waveguide substrate 20 bonded with the second substrate 10. The V-groove 21 has a vertical face and the first reflective face 21M with a tilt angle of 45 degrees. Then the V-groove 21 is as deep as to reach the core 23.

Figure 1:
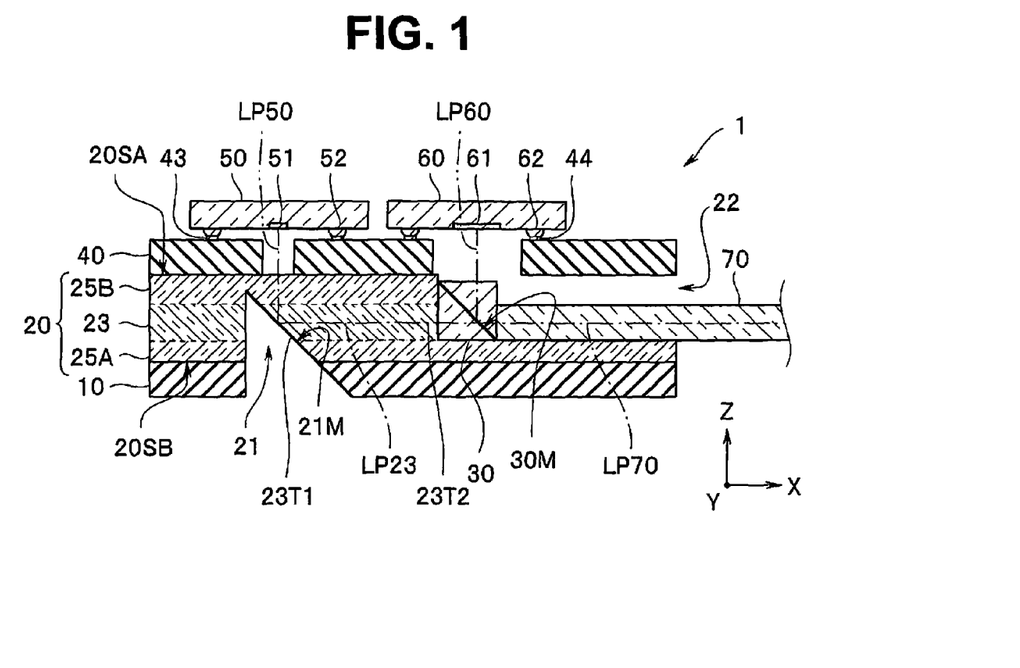
FIG. 1 is a cross-section view of an optical transmission module according to a first embodiment.

FIG. 1 illustrates that the core 23 is extended to the end face of the optical waveguide substrate 20 and the groove 22 splits the core 23 to form the first reflective face 21M. Thus, the core 23 and the clad 25 are exposed also on the vertical faces of the groove 22 as on the first reflective face 21M. However, the core 23 may be extended to the position of the first reflective face 21M of the V-groove 21 and all the vertical faces of the groove 22 may be the exposed faces of the clad.

Figure 5F:
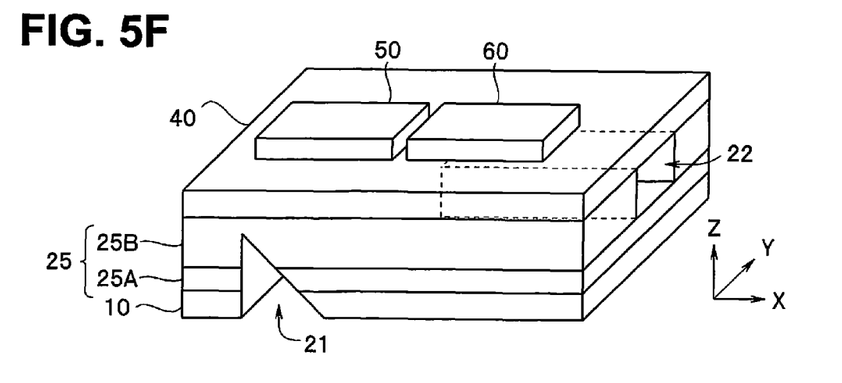
FIG. 5F is a perspective view for explaining the method for manufacturing the optical transmission module according to the first embodiment.

<Step S17>FIG. 5F

The first substrate 40 is bonded to the main surface 20SA of the optical waveguide substrate 20. That is, the first substrate 40 as wiring board mounted with the light emitting device 50 and the light receiving device 60 thereon is provided on the upper surface 20SA of the optical waveguide substrate 20. The upper surface of the groove 22 is covered with the first substrate 40 to be a hole.

Figure 5G:
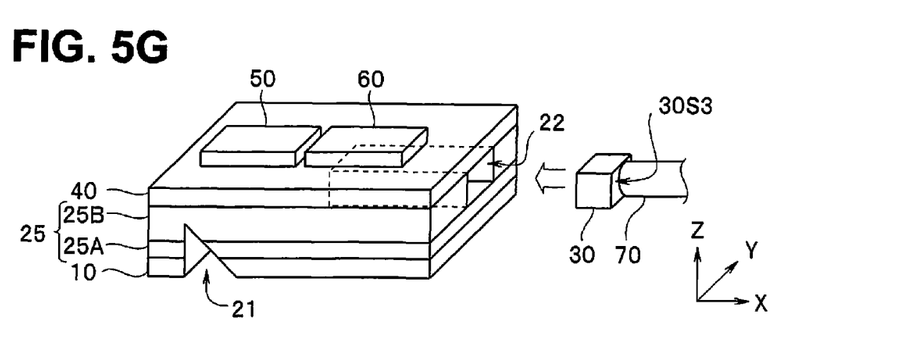
FIG. 5G is a perspective view for explaining the method for manufacturing the optical transmission module according to the first embodiment.

<Step S18>FIG. 5G

The optical fiber 70 is bonded to the prism 30. For example, the multimode-type optical fiber 70 with a diameter of 125 µm is configured of a core 71 with a diameter of 50 µm for transmitting a light, and a clad 72 for covering the outer periphery of the core 71. The optical fiber 70 may be covered with a resin-made outer coat.

The cuboid prism 30 has an upper face 30SU, a lower face 30SD, and four side faces 30S1 to 30S4. Then, the third side face 30S3 of the prism 30 is bonded to an end face of the optical fiber 70 by a light-transmissive ultraviolet cure adhesive or the like. The second reflective face 30M with a tilt angle of 45 degrees of the prism 30 reflects the second light with the second wavelength upward. On the other hand, the second reflective face 30M transmits a light with the first wavelength.

<Step S19>

The prism 30 bonded with the optical fiber 70 is inserted from the opening on the side of the groove 22 and fixed on the groove 22 by a transparent ultraviolet cure adhesive (not illustrated), for example. At this time, as illustrated in FIG. 6, the first side face 30S1 of the prism 30 is arranged to contact the first wall face 23S1 of the groove 22 and the second side face 30S2 is arranged to contact the second wall face 24S1 orthogonal to the first wall face 23S1.

Not only the first resin of the core 23 and the positioning member 24 but also the second resin of the clad is exposed on the first wall face 23S1 and the second wall face 24S1 of the groove 22. It may not be easy to do the patterning such that the exposed face of the first resin and the exposed face of the second resin form perfectly the same planes.

Thus, it is preferable that the groove 22 is patterned such that the core 23 and the positioning member 24 are convex.

Figure 6:
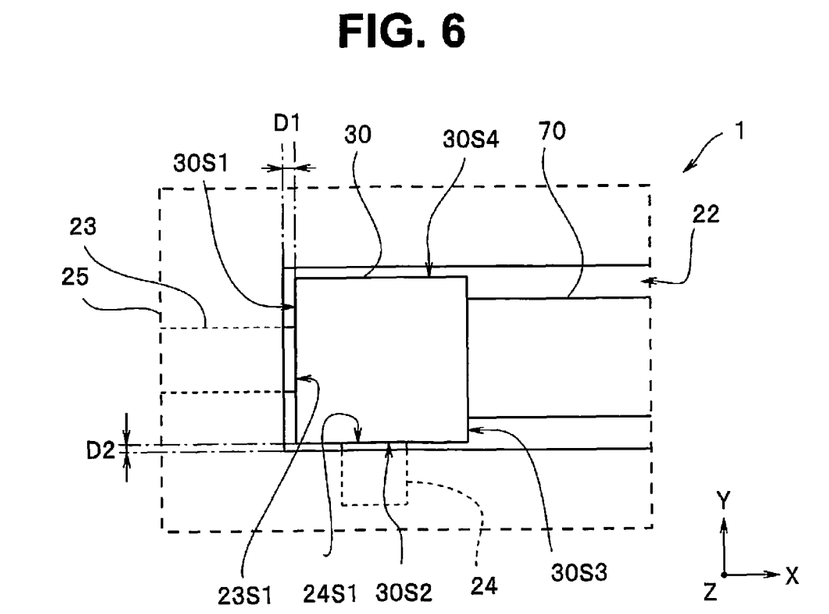
FIG. 6 is a top view of essential parts in the optical transmission module according to the first embodiment.

For example, in the optical transmission module 1 illustrated in FIG. 6, the first wall face 23S1 of the groove 22 which the side face 30S1 of the prism 30 contacts is a convex part with a height D1 formed of the core 23. Further, the second wall face 24S1 of the groove 22 which the side face 30S2 of the prism 30 contacts is a convex part with a height D2 formed of the positioning member 24. The heights D1 and D2 of the convex parts in a range of 0.5 pm to 5µm can accurately arrange the prism 30.

The core 23 and the positioning member 24 are accurately positioned by photolithography. Therefore, the two side faces of the prism 30 contact the second end face 23S1 of the core 23 and the face 24S1 of the positioning member 24 so that the prism 30 can be easily and accurately defined at a position in the horizontal direction (XY direction).

With the manufacturing method according to the present embodiment, it is possible to easily manufacture the optical transmission module 1 with excellent optical transmission efficiency.

The optical transmission module 1 is such that the first optical device is the light emitting device 50 and the second optical device is the light receiving device 60. However, the same effects as the optical transmission module 1 can be obtained even when the first optical device is a light receiving device and the second optical device is a light emitting device. Further, both the first optical device and the second optical device may be a light receiving device or a light emitting device.

Modification of First Embodiment

An optical transmission module 1A according to a modification of the first embodiment will be described below. The optical transmission module 1A is similar to the optical transmission module 1, and thus the same components are denoted with the same reference numerals and the description thereof will be omitted.

Figure 7:
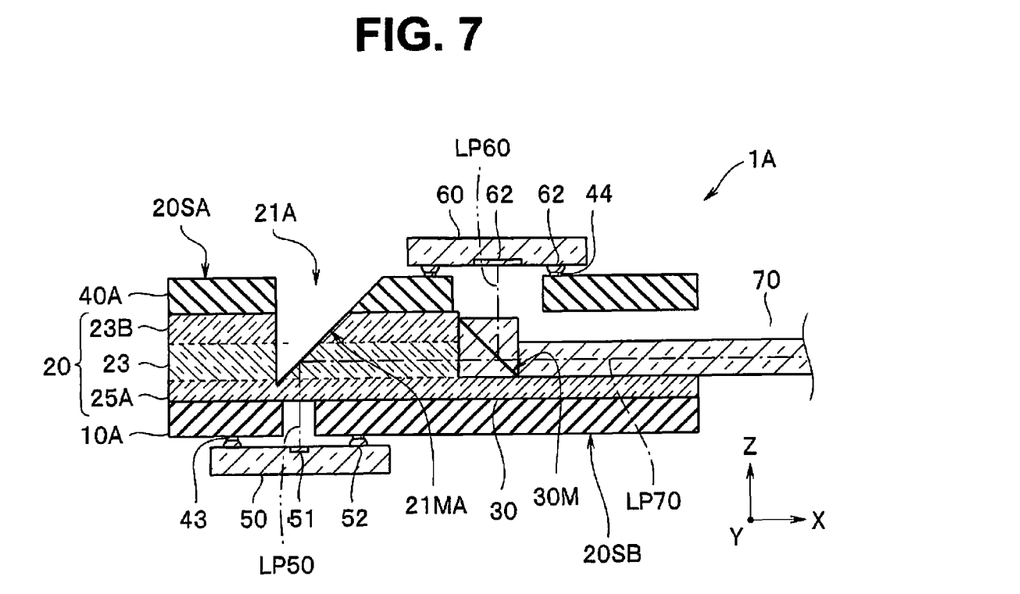
FIG. 7 is a cross-section view of an optical transmission module according to a modification of the first embodiment.

As illustrated in FIG. 7, in the optical transmission module 1A, a first substrate 40A mounted with the light receiving device 60 thereon is provided on the upper face 20SA of the optical waveguide substrate 20, and a second substrate 10A mounted with the light emitting device 50 thereon is provided on the lower surface 20SB of the optical waveguide substrate 20. That is, in the optical transmission module 1A, the second substrate 10A is a wiring board providing the electrode pads 43 thereon.

A first reflective face 21MA with a tilt angle of 45 degrees relative to the first end face of the core 23 is a tilt face with a tilt angle of 45 degrees of a groove 21A formed from the upper surface by use of a dicing blade. The first reflective face 21MA reflects a light incident vertically to the core 23 from below in the longitudinal direction of the core 23.

The optical transmission module 1A has the same effects as the optical transmission module 1.

Of course, an optical transmission module in which the light emitting device 50 is mounted on the first substrate 40A and a light receiving device 60A is mounted on the second substrate 10A has the same effects as the optical transmission module 1A.

Second Embodiment

An optical transmission module 1B according to a second embodiment will be described below. The optical transmission module 1B is similar to the optical transmission module 1, and thus the same components are denoted with the same reference numerals and the description thereof will be omitted.

Figure 8:
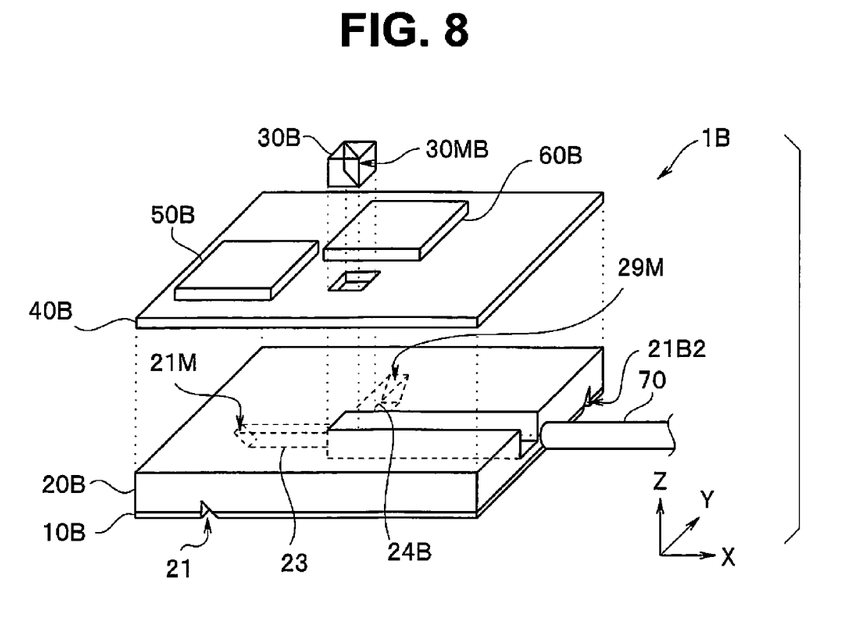
FIG. 8 is an exploded view of an optical transmission module according to a second embodiment.
Figure 9:
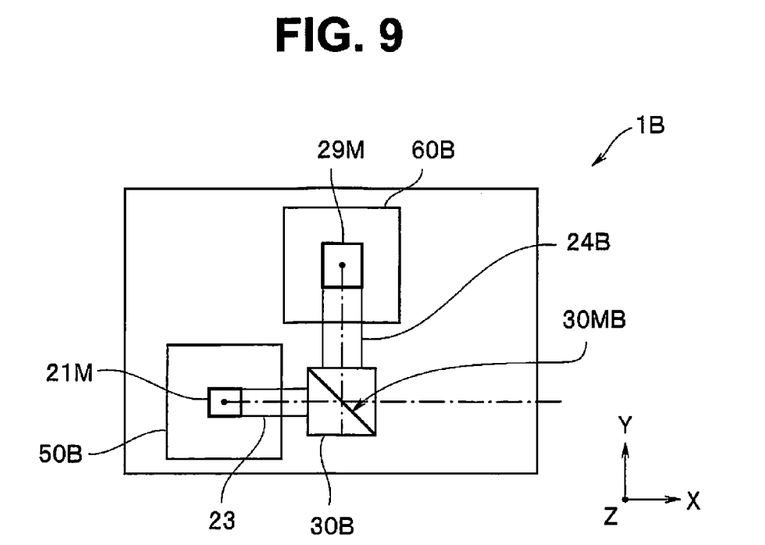
FIG. 9 is a top view for explaining optical paths in the optical transmission module according to the second embodiment.

As illustrated in FIG. 8 and FIG. 9, in the optical transmission module 1B, a second reflective face 30MB of a prism 30B reflects the second optical signal guided by the optical fiber 70 in the in-plane orthogonal direction (Y direction). Further, a positioning member extended to be elongated has the optical waveguide function and configures a second core 24B. A third reflective face 29M with a tilt angle of 45 degrees is present relative to an end face of the second core 24B. The third reflective face 29M is a wall face of a V-groove 21B2 having a tilt face with a tilt angle of 45 degrees, which is formed by a dicing blade from the lower surface (the second substrate) of an optical waveguide substrate 20B. That is, the V-groove 21B2 is parallel with the groove 22 and orthogonal to the V-groove 21.

A light emitting device 50B is provided immediately above the core 23, and a light receiving device 60B is provided immediately above the second core 24B which is a positioning member extended to be orthogonal to the core 23.

Thus, the second optical signal guided by the optical fiber 70 is reflected on the second reflective face 30MB of the prism 30B to be guided to the second core 24B, and is then reflected on the third reflective face 29M to be incident into the light receiving device 60B. In other words, the light receiving device 60B is optically coupled with the optical fiber 70 via the third reflective face 29M, the second core 24B, and the second reflective face 30MB of the prism 30.

In the optical transmission module 1B, the second core 24B as positioning member is formed to oppose the positioning member 24 in the optical transmission module 1. However, two side faces and the bottom face of the prism 30B are easy to arrange with high accuracy like the prism 30, and the optical transmission module 1B has the same effects as the optical transmission module 1, and is higher in a degree of freedom in arrangement of the optical devices and easier to downsize (shorten, in particular) than the optical transmission module 1.

Of course, the same effects as the optical transmission module 1B can be obtained even when the first optical device is a light receiving device and the second optical device is a light emitting device. Further, both the first optical device and the second optical device may be a light receiving device or a light emitting device.

The present embodiment is such that the prism 30 is inserted from the opening formed on a first substrate 40B to be fixed and the optical fiber 70 is inserted from the groove 22 to be fixed, but the prism 30 and the optical fiber 70 may be bonded and fixed, and then inserted from the groove 22 to be fixed. Further, the opening having the same shape as in the groove 22 may be formed on the first substrate 40B, and the prism 30 and the optical fiber 70 which are bonded may be arranged on the first substrate 40B to be fixed.

Third Embodiment

An endoscope 9 according to a third embodiment will be described below.

Figure 10:
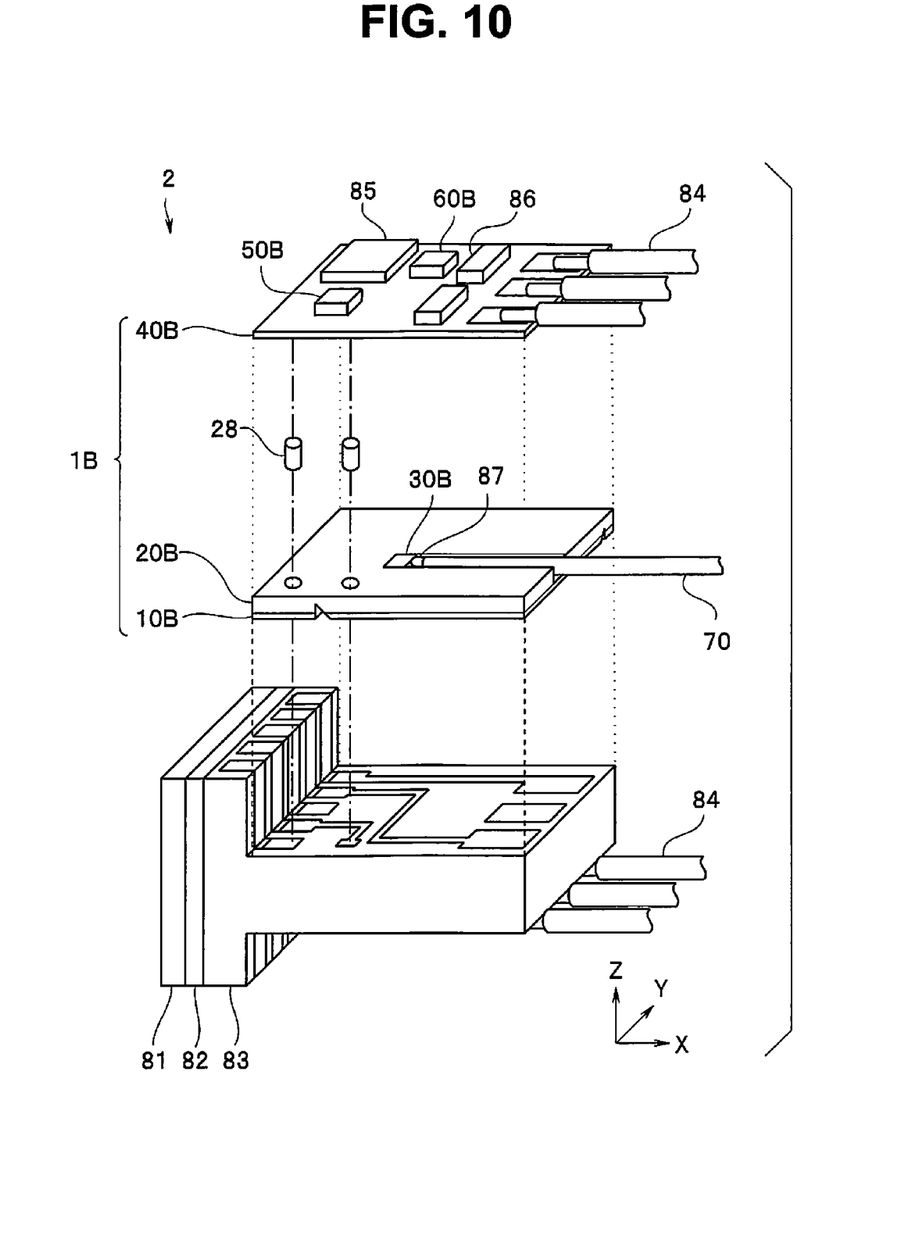
FIG. 10 is an exploded view of an image pickup module in an endoscope according to a third embodiment.

At first, FIG. 10 illustrates an image pickup module 2 including the optical transmission module 1B. The image pickup module 2 has a cover glass (glass lid) 81, an image pickup device 82, a T-shaped wiring board 83, the optical transmission module 1B, and a cable 84. The T-shaped wiring board 83 is mounted with the image pickup device 82, and is further connected with the cable 84. Not only the light emitting device 50B and the light receiving device 60B but also an electronic part 86 such as semiconductor IC (85) or chip capacitor is surface-mounted on the first substrate 40B in the optical transmission module 1B having the wave coupling/branching function. A ball lens 87 for collecting lights is provided at an end face of the optical fiber 70 in the optical transmission module 1B.

The optical transmission module 1B is provided on the image pickup device 82 and the wiring board 83 for transmitting/receiving an electric signal. The first wiring board 40B in the optical transmission module 1B is connected with the wiring board 83 by a pass-through wiring 28 passing through the optical waveguide substrate 20B and a second wiring board 10B.

In the optical transmission module 1B, the second optical signal guided via the optical fiber 70 is received by the light receiving device 60B and converted to an electric signal to be transmitted to the image pickup device 82. On the other hand, an image pickup signal from the image pickup device 82 is converted to the first optical signal by the light emitting device 50B and guided via the optical fiber 70. For example, a clock signal converted to the second optical signal with the wavelength λ2 is incident from the optical fiber 70 into the optical transmission module 1B including a wave coupling/branching instrument to be received by the light receiving device 60B. The received second optical signal is photoelectrically converted to an electric signal and is input as clock signal into the image pickup device 82. On the other hand, the image pickup signal output from the image pickup device 82 is converted to the first optical signal with the wavelength λ1 by the light emitting device 50B, and is guided to the optical fiber 70.

The image pickup module 2 optically converts and multiplexes the input/output signals of the image pickup device 82 by the optical transmission module 1B having the small wave coupling/branching function, thereby being easily downsized.

Figure 11:
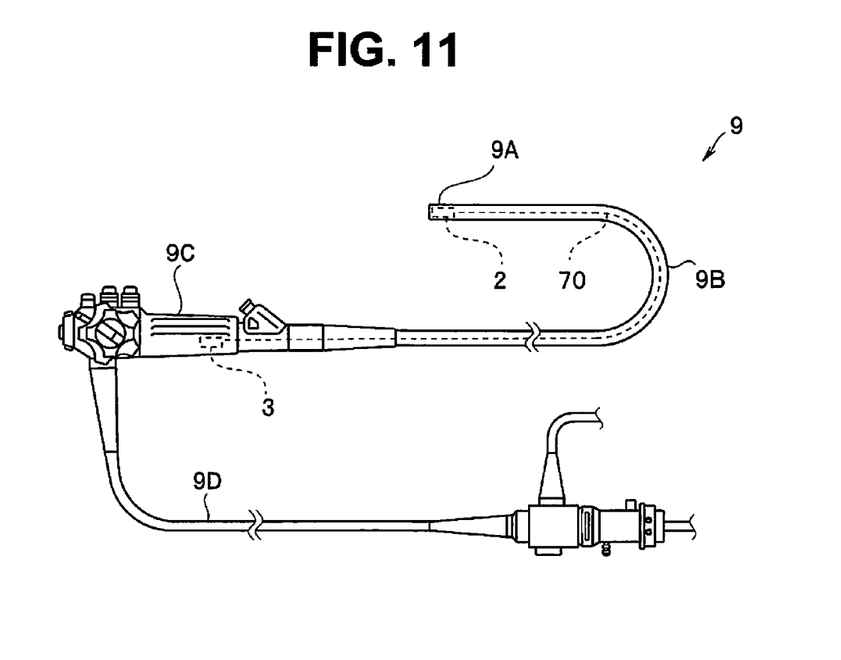
FIG. 11 is a perspective view of the endoscope according to the third embodiment.

As illustrated in FIG. 11, the endoscope 9 includes an insertion portion 9B in which the image pickup module 2 is provided at a distal end portion 9A, an operation part 9C provided at the base of the insertion portion 9B, and a universal cord 9D extending from the operation part 9C. An optical signal guided by the optical fiber 70 inserted through the insertion portion 9B is converted to an electric signal by the image pickup module 2 provided in the operation part 9C.

The endoscope 9 has the small image pickup module 2, and thus the distal end portion 9A has a small diameter.

The present invention is not limited to the embodiments and modification, and can be variously changed, combined, and applied within the scope without departing from the spirit of the invention.

What is claimed is:

1. An optical transmission module comprising:
   a first optical device for transmitting or receiving a first optical signal;
   a second optical device for transmitting or receiving a second optical signal;
   an optical fiber for guiding a third optical signal in which the first optical signal and the second optical signal are coupled; and
   an optical waveguide substrate having an optical waveguide made of first resin, in which the optical waveguide has a first reflective face with a tilt angle of 45 degrees relative to a first end face, and a second end face is optically coupled with an optical path of the optical fiber,
   wherein a groove formed on the optical waveguide substrate is provided with the optical fiber and a prism having a second reflective face with a tilt angle of 45 degrees through which the first optical signal transmits,
   an optical path of the optical waveguide is optically coupled with an optical path of the first optical device orthogonal to the optical path of the optical waveguide via the first reflective face,
   the optical path of the optical fiber is optically coupled with an optical path of the second optical device orthogonal to the optical path of the optical fiber via the second reflective face,
   the second end face of the optical waveguide is exposed on a first wall face of the groove, and a face of a positioning member made of the first resin is exposed on a second wall face of the groove, and
   a first side face of the prism contacts the first wall face of the groove, and a second side face contacts the second wall face of the groove.

2. The optical transmission module according to claim 1, wherein the first side face contacts a convex part of the optical waveguide, and the second side face contacts a convex part of the positioning member.

3. The optical transmission module according to claim 2, wherein a first substrate mounted with the first optical device and the second optical device thereon is provided on an upper surface of the optical waveguide substrate.

4. The optical transmission module according to claim 2, wherein a first substrate mounted with the first optical device thereon is provided on an upper surface of the optical waveguide substrate, and a second substrate mounted with the second optical device thereon is provided on a lower surface of the optical waveguide substrate.

5. The optical transmission module according to claim 1, wherein the first optical device and the second optical device are provided immediately above or immediately below the optical waveguide, respectively.

6. The optical transmission module according to claim 1, wherein the first optical device is provided immediately above or immediately below the optical waveguide, the positioning member configures a second optical waveguide which is extended to be orthogonal and which has a third reflective face with a tilt angle of 45 degrees relative to an end face, and the second optical device provided immediately above the second optical waveguide is optically coupled with the optical fiber via the third reflective face, the second optical waveguide, and the prism.

7. The optical transmission module according to claim 1, wherein the first optical device is a light emitting device, and the second optical device is a light receiving device.

8. The optical transmission module according to claim 1, wherein the first optical device and the second optical device are each a light emitting device.

9. The optical transmission module according to claim 1, wherein the first optical device and the second optical device are each a light receiving device.

10. An endoscope comprising the optical transmission module according claim 1 at a distal end portion of an insertion portion.

11. A method for manufacturing the optical transmission module according to claim 1, comprising the step of:

patterning the optical waveguide and the positioning member at a same time by the photolithography method.

12. The method for manufacturing the optical transmission module according to claim 11, wherein a step of providing the prism bonded with the optical fiber at a predetermined position in the groove after a step of bonding the optical fiber to the prism.

* * * * *